United States Patent [19]

Fráter et al.

[11] Patent Number: 5,151,411
[45] Date of Patent: Sep. 29, 1992

[54] TRICYCLIC KETONES AND FRAGRANCE COMPOSITIONS CONTAINING SAME

[75] Inventors: Georg Fráter, Uster; Daniel Helmlinger, Gockhausen, both of Switzerland

[73] Assignee: Givaudan Corporation, Clifton, N.J.

[21] Appl. No.: 747,816

[22] Filed: Aug. 20, 1991

[30] Foreign Application Priority Data

Aug. 24, 1990 [CH] Switzerland .................... 2756/90

[51] Int. Cl.$^5$ .............................................. A61K 7/46
[52] U.S. Cl. ...................... 512/15; 568/354; 568/373
[58] Field of Search ............ 512/15, 13; 568/354, 568/373

[56] References Cited

U.S. PATENT DOCUMENTS

| | | | |
|---|---|---|---|
| 2,914,565 | 11/1959 | Ohloff | 512/13 |
| 3,029,255 | 4/1962 | Stoll | 512/13 |
| 3,050,532 | 8/1962 | Schumacher et al. | 512/13 |
| 3,427,328 | 2/1969 | Sandermann et al. | 512/13 |
| 4,124,642 | 11/1978 | Buchi et al. | 512/15 |

FOREIGN PATENT DOCUMENTS

| | | | |
|---|---|---|---|
| 165458 | 12/1985 | European Pat. Off. | 512/15 |
| 0315895 | 11/1988 | European Pat. Off. | 512/15 |
| 2461593 | 3/1977 | Fed. Rep. of Germany | 512/15 |
| 8204293 | 9/1983 | France | 512/15 |
| 2065108 | 6/1981 | United Kingdom | 512/15 |

OTHER PUBLICATIONS

A. Saito et al., Chem. Lett., (1983) 729–732.
G. Lucius, Angew. Chem., 68 (1956) 247.

*Primary Examiner*—James H. Reamer
*Attorney, Agent, or Firm*—Robert F. Tavares; Linda A. Vag

[57] ABSTRACT

A compound of the formula

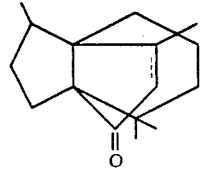

I wherein the dotted line signifies an optional bond, as racemates or individual enantiomers, odorant compositions containing the same, and a process for the manufacture of the compounds of formula I which comprises rearranging sclareolide, episclareolide or isosclareolide at an elevated temperature in acidic medium with dehydration and, if desired, reducing the carbon-carbon double bond present in the reaction product.

22 Claims, No Drawings

TRICYCLIC KETONES AND FRAGRANCE COMPOSITIONS CONTAINING SAME

SUMMARY OF THE INVENTION

The invention concerns novel tricyclic ketones, namely propellanes of formula I,

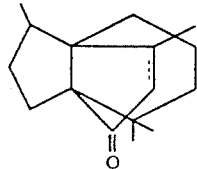

I wherein the dotted line represents an optional bond. Formula I is intended to particularly embrace as racemates or individual enantiomers, formulas I', I" and I'".

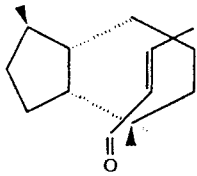

I'

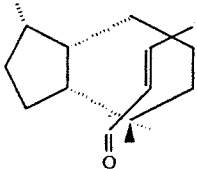

I"

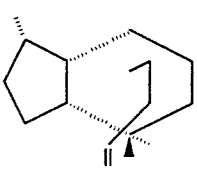

I'"

The ketones of formula I are amber odorants distinguished by powerful, diffuse and very natural woody, cedar-like, amber-like notes with fruity olfactory aspects. The invention therefore also concerns the use of the formula I ketones as odorants.

DESCRIPTION OF THE PREFERRED EMBODIMENTS

The ketones of formula I can be prepared by the rearrangement of sclareolide II at an elevated temperature in acidic medium with dehydration and, if desired, reduction of the carbon-carbon double bond present in the product. The term "sclareolide II" is intended to embrace the following compounds:

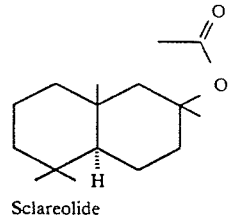

Sclareolide

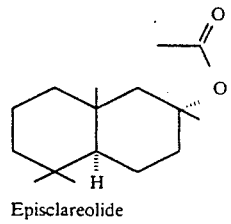

Episclareolide

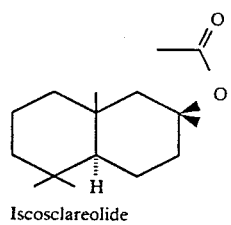

Iscosclareolide

The following are suitable process parameters:

| | Rearrangement with dehydration |
|---|---|
| Temperature: | elevated, e.g. 70–120° C., especially temperatures about 100° C. |
| Working-up: | addition of water, extraction with organic solvent |
| Solvent: | the phosphorus-containing rearrangement agent (e.g. polyphosphoric acid, P$_2$O$_5$/methanesulphonic acid) used in excess fullfils this function. |
| | Reduction |
| Temperature: | elevated, e.g. about 50–100° C., especially about 80° C. to about 100° C. |
| Solvent: | e.g. toluene |
| Working-up: | alkaline treatment in the presence of an organic solvent, washing, e.g. stirring with 2N NaOH and ether, washing the organic phase with 2N HCl and saturated sodium chloride solution |

The tricyclic ketones of formula I are distinguished by powerful, diffuse and very natural woody, cedar-like, amber-like notes with fruity olfactory aspects. The most interesting compound is I'" (most pronounced amber note), followed by I' and I".

On the basis of their natural olfactory notes the compounds of formula I are especially suitable for modifying known compositions. They combine with numerous known odorant ingredients of natural or synthetic origin, whereby the range of the natural raw materials can embrace not only readily-volatile but also moderately-volatile and difficultly-volatile components and that of the synthetics can embrace representatives from practically all classes of substances, as is evident from the following compilation:

Natural products such as tree moss absolute, basil oil, citrus oils (such as bergamot oil, mandarin oil, etc.), mastix absolute, myrtle oil, palmarosa oil, patchouli oil, petitgrain oil Paraguay, wormwood oil, alcohols such as farnesol, geraniol, linalool, nerol, phenylethyl alcohol, rhodinol, cinnamic alcohol, aldehydes such as citral, Cetonial TM (Givaudan), α-methyl-3,4-methylene-dioxyhydrocinnamaldehyde) α-hexylcinnamaldehyde, hydroxycitronellal, Lilial ® (Givaudan) (p-tert.butyl-α-methyl-dihydrocinnamaldehyde), methylnonylacetaldehyde, ketones such as allylionone, α-ionone, β-ionone, isoraldein (isomethyl-α-ionone), methylionone, esters such as allyl phenoxyacetate, benzyl salicylate, cinnamyl propionate, citronellyl acetate, citronellyl ethoxalate (citronellyl . O—CO—CO . OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, lactones such as γ-undecalactone, various components often used in perfumery such as musk ketone, indole, p-menthane-8-thiol-3-one, methyleugenol.

Worthy of mention is, further, the manner in which the ketones of formula I round-off and harmonize the olfactory notes of known compositions without, however, dominating in an unpleasant manner. Thus, they underline the yellow sandalwood and leather notes in perfume bases, e.g. with a chypre, tobacco, amber, leather, oriental and spicy character. Moreover, they confer fullness and warmth to the composition.

The ketones of formula I (or mixtures thereof) can be used in wide limits which can extend in compositions, for example, from 0.1% (detergents)-5%(alcoholic solutions), without these values being, however, limiting values, since the experienced perfumer can also achieve effects with even lower concentrations or can sythesize novel complexes with even higher amounts. The preferred concentrations range between about 0.2% and 2%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The ketones of formula I can accordingly be used in the manufacture of compositions and, as will be evident from the above compilation, a wide range of known odorants or odorant mixtures can be used. In the manufacture of such compositions the known odorants enumerated above can be used according to methods known to the perfumer, such as e.g. from W. A. Poucher, Perfumes, Cosmetics and Soaps 2, 7th Edition, Chapman and Hall, London, 1974.

The compounds referred to by way of formulas in the following Examples are as follows:

| | |
|---|---|
| (−)I′ | 1S,6R,10R-5,5,9,10-Tetramethyl-tricyclo[4,3,3,-0$^{1,6}$]dodec-8-en-7-one |
| (−)I″ | 1S,6R,10S-5,5,9,10-Tetramethyl-tricyclo[4,3,3,-0$^{1,6}$]dodec-8-en-7-one |
| (−)VII | 3,3a,4,5,5a,6,7,8,8,9,9a,-Decahydro-6,6,9a-trimethyl[3aS-(3aα,5aβ,9aα)]-2H-benz[e]inden-2-one |
| (−)VIII | 1,4,5,5a,6,7,8,9,9a,9b-Decahydro-6,6,9a-trimethyl-[5aS-(5aβ,9aα,9bβ)]-2H-benz[e]inden-2-one |
| (−)I‴ | 1S,6R,9S,10S-5,5,9,10-Tetramethyl-tricyclo-[4,3,3,0$^{1,6}$]dodecan-7-one |
| X | 2aR,3R,5aR,2a,3,6,6-Tetramethyl-2a,3,4,5,5a,6,7,-8-octahydro-1(2H)-acenaphthylenone |
| XI | 1S,6R,10S-9-Methylene-5,5,10-trimethyl-tricyclo-[4,3,3,0$^{1,6}$]dodec-7-ene |

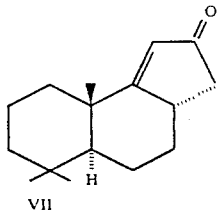

VII

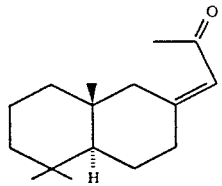

VIII

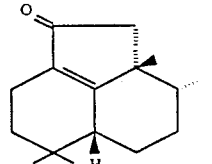

X

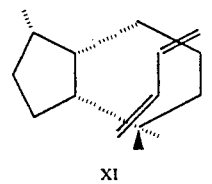

XI

ILLUSTRATION OF THE PREFERRED EMBODIMENTS

EXAMPLE 1

Polyphosphoric acid (150 g) is heated to 100° C. (+)-Sclareolide II′(decahydro-3a,6,6,9a-tetramethyl-[3aR(3aα,5aβ,9aα,9bβ)]naphto[2,1-b]furan-2 (IH)-one) (40 g) is now added rapidly and the mixture is stirred at 100° C. for 1 hour. The mixture is then cooled to 0° C., stirred for 1¼ hours with 100 ml of water and 50 ml of hexane and extracted with hexane. The organic phase is washed with saturated bicarbonate solution and with saturated sodium chloride solution, dried and evaporated. Crude product (30.8 g) is obtained in this manner. This product contains (GC) 15% (−)I′, 44% (−)I″, 4.5% (−)VII, 25% (−)VIII. A distillation yields 16.6 (45%) of a mixture of (−)I′ and (−)I″ in the ratio 1/3.3 (b.p. 81-89/1.1@10$^{-5}$ Torr) and 8.2 g (22%) of a mixture of (−)VII and (−)VIII in the 1/5.4.

The individual compounds (−)I′, (−)I′, (−)VII and (−)VIII can be purified by chromatography (silica gel 60, 230-400 mesh, elution with 20% ether in hexane).

Spectral data and olfactory properties:

Compound (−)I′

IR: (liq) 1690, 1615 cm$^{-1}$. UV (CH$_2$Cl$_2$) λ max: 235, ε=9913. $^1$H-NMR (200 MHz, CDCl$_3$): 5.97 (m,J=1.2,H-C(8)); 2.07 (d,J=1.2,CH$_3$-C(9)); 1.03 (s,CH$_3$-C(5)); 0.95 (d,J=7,CH$_3$-C(10)); 0.79 (s,CH$_3$-C(5); 13$_C$NMR (CDCl$_3$) 214.1 (s,C(7)); 181.2 (s,C(9)); 132.6 (d,C(8)); 65.3 (s,C(6)); 57.6 (s,C(1)); 43.1 (d,C(10)); 34.9 (s,C(5)); 33 (t,C(4)); 31.2 (t,C(11)); 30.9 (t,C(12)); 28 (q,C(13)); 27.4 (q,C(14)); 26.3 (t,C(2)); 17.1 (q,C(15)); 16.5 (t,C(3)); 16.4 (q,C(16)); MS: 232 (40,M$^{30}$), 217(12), 204(2), 189(6), 175(12), 161(14), 150(100), 135(11), 122(34), 105(14), 91(15), 77(11), 69(8), 55(9), 41(17).

Compound (−)I″

IR (liq): 1690, 1620 cm$^{-1}$. UV (EtOH) λ max: 235, ε=8754 $^1$H-NMR (200 MHz, CDCl$_3$): 5.76(m,J=1.3,H-C(8)); 2.05 (d,J=1.3, CH$_3$-C(9)); 1.05 (s,CH$_3$-C(5)eq); 1.00 (d,J=7,CH$_3$-C(10)); 0.84 (s,CH$_3$-C(5)ax); $^{13}$C-NMR (CDCl$_3$): 213.8 (s,C(7)); 182.9 (s,C(9)); 129.1 (d,C(8)); 65.5 (s,C(6)); 58.9 (s,C(1)), 44.1 (d,C(10)); 34.8 (s,C(5)); 33.8 (t,C(4)); 31.8 (t,C(11)); 28.4 (t,C(12)); 26.9 (q,C(14)); 26.3 (q,C(13)); 22.9 (t,C(2)); 17.9 (t,C(3)); 15.8 (q,C(16)); 15.4 (q,C(15)); MS: 232 (34 M+), 217(11), 204(6), 189(6), 175(16), 161(15), 150(100), 135(17), 122(37), 105(15), 91(16), 77(10), 69(10), 55(11), 41(21), 28(52), [α]$_D^{20}$=−145.58° (CHCl$_3$, c=1.047). Odor of (−)I″: woody, cedar-like, fruity, amber-like.

Compound (−)VII

IR (CHCl$_3$) 1680, 1600 cm$^{-1}$. UV (EtOH) λmax: 232, ε=11851. $^1$H-NMR (CDCl$_3$): 5.695–5.68 (m,H-C(1)); 2.96–2.88 (m,Hα-C(3a)); 2.545 (dd,J=19,J=6.8,Hα-C(3)); 2.29–2.22 (m,Hα-C(4); 1.95 (dd,J=19,J=2,Hβ-C(3)); 1.18 (s,CH$_3$-C(9a)); 0.93 (s,CH$_3$-C(6)); 0.895 (s,CH$_3$-C(6)); $^{13}$C-NMR (CDCl$_3$): 194.5 (s,C(2)); 121.9 (d,C(1)); 53.67 (d,C(5a)); 42.4 (t,C(3)); 41.8 (t,C(7)); 39.9 (s,C(9a)); 38.3 (d,C(3a)); 37.0 (t,C(9)); 35.8 (t,C(4)); 33.9 (s,C(6)); 33.3 (q,C(11)); 21.7 (q,C(10)); 21.3 (t,C(5)); 19.3 (q,C(12)); 18.4 (t,C(8)); MS: 232 (57 M+), 217(12), 190(30), 175(30), 161(12), 147(19), 135(19), 122(26), 109(100), 91(40), 79(26), 69(27), 55(46), 41(77), 28(19). [α]$_D^{20}$=−191.8 (c=1.23 CHCl$_3$). Odor of (−)VII: slightly woody, camphoraceous.

Compound (−)VIII

IR (liq): 1705, 1670, 1620. UV: λ max: 235, ε=14935, CH$_2$Cl$_2$. $^1$H-NMR (CDCl$_3$ 400 MHz): 5.83 (m,J=1.4,H-C(3)); 2.85 (ddd,J=14.6,J=1.4,J=4.8,H-C(4)); 2.48 (d(broad), J=6,H-C(9b)); 2.32 (dd(broad),J=7,J=12.5,H-C(4)); 2.23 (ddd,J=19,J=6.5,J=1,Hb-C(1)); 2.15 (ddd,J=19,J=1, J=2.5,Hα-C(1)); 1.91(ddd,J=13.4,J=2.4,J=6.4,Heq-C(5)); 1.27 (dd,J=12.5,J=2.6,H-C(5a)); 0.95 (s,H$_3$C(11); 0.86 (s,H$_3$-C(10)); 0.67 (s,H$_3$-C(12)) $^{13}$C-NMR (CDCl$_3$): 208.2 (s,C(2)); 181.7 (s,C(3a)); 126.7 (d,C(3)); 54.7 (d,C(9b)); 52.5 (d,C(5a)); 41.4 (t,C(7)); 39.5 (t,C(9)); 38.3 (s,C(9a)); 35.4 (t,C(1)); 32.8 (q,C(11)); 32.5 (s,C(6)); 30.0 (t,C(4)); 21.9 (t,C(5)); 21.1 (q,C(10)); 18.0 (t,C(8)); 12.0 (q,C(12)) MS: M+ 232(11); 217(9); 204(5); 199(1); 189(5.6); 175(4.4); 161(8.4); 149(10); 137(72); 123(38); 109(57); 96(100); 91(16); 81(40); 69(33.5); 55(29); 41(48) [α]$_D^{20}$=−103.5° (c=1.04 CHCl$_3$). Odor of VIII: slightly woody.

EXAMPLE 2

Firstly, 24 g of phosphorous pentoxide are dissolved in 240 g of methanesulphonic acid and 50 g of (+)-sclareolide II′ are heated at 106° C. in 250 g of this solution for 20 minutes. The mixture is stirred at 104° C. for a further 30 minutes. It is then cooled with an ice bath, treated with ice-water and extracted with ether. The organic phase is washed with 2 NaOH, washed with saturated sodium chloride solution, dried and evaporated. The crude product (31.5 g) is distilled. Two fractions are obtained in this manner. The lower-boiling fraction, b.p. 115°–126° C. (0.045 mm), 9.5 g (20%), contains (GC) 3% (−)I′, 13% (−)I″, 8.4% (−)X, 19% (−)VII and 50% (−)VIII. The higher-boiling fraction, 119°–126° C. (0.045), 11.5 g (25%), contains (GC) 26% (−)VII and 70% (−)VIII.

Compound X can be purified by chromatography on silica gel 60 (0.04–0.063 mm).

Spectral data of X

IR (KBr): 1695, 1640 cm$^{-1}$. UV (EtOH) λ max: 242.4, ε=13025 (purity 75%). $^1$H-NMR (400 MHz) CDCl$_3$: 2.51 (d,J=18.5,Hε-C(2)); 1.99 (d,J=18.5,Hα-C(2)); 1.74 (m,Heq-C(5)); 1.32 (s,H$_3$-C(9)); 0.95 (s,H$_3$-C(12)); 0.87 (s,H$_3$-C(11)); 0.78 (s,d,J=7, H$_3$-C(10)) . $^{13}$C-NMR (CDCl$_3$): 206.7 (s,C(1)); 179.4 (s,C(8b)); 134.8 (s,C(8a)); 47.4 (t,C(2)); 44.3 (s,C(2a)); 42.9 (d,C(5a)); 37.4 (d,C(3)); 33.8 (t,C(7)); 31.5 (s,C(6)); 28.0 (t,C(4)); 27.6 (q,C(12)); 26.5 (q,C(9)); 23.8 (t,C(11)); 22.0 (t,C(5)); 16.7 (t,C(8)); 14.45 (q,C(10)). MS: 232(100); 217(28); 203(4); 180(28); 176(55); 161(45); 148(43); 134(47); 119(31); 105(38); 91(50); 77(22); 69(15) 65(11); 55(20); 41(37); 29(8).

EXAMPLE 3

Polyphosphoric acid (15 g) is heated to 100° C. (−)Isosclareolide II‴,(decahydro-3a,6,6,9a-tetramethyl[-3aS(3aβ,5aβ,9aα,9bβ)]naphtho[2,1-b]furan-2(1H)-one) (4 g) is added and the mixture is stirred at 100° C. for 15 minutes. It is then poured into water, extracted with methylene chloride, washed neutral and evaporated. The crude product (3 g) is eluted over 150 g of silica gel with 20% and 50% hexane/ether. In this manner there is obtained 0.74 g (20%) of a mixture of (−)I′/I″ in the ratio 16/84 and 0.384 g (10%) of (−)VII and (−)VIII in the ratio 5/92.

EXAMPLE 4

Polyphosphoric acid (11.3 g) is heated to 100° C. (−)Episclareolide II″(decahydro-3a,6,6,9a-tetramethyl[3aR(3aα,5aβ,9aα,9bα]naphtho[2,1-b]furan-2(1H)-one) (3 g) is added and the mixture is stirred at this temperature for 15 minutes. It is then poured into water, extracted with methylene chloride, washed neutral and evaporated. The crude product (1.9 g) is eluted over 100 g of silica gel with 20% and 50% hexane/ether. In this manner there are obtained 359 mg (12.9%) of I′ and I″ in the ratio 43/56 and 180 mg (6%) of VII and VIII in the ratio 9/87.

EXAMPLE 5

Lithium aluminium hydride (150 mg) is added to 1 g of a mixture of (−)I′/I″ in the ratio ⅓ dissolved in 10 ml of ether. The mixture is then stirred at room temperature for 20 hours. The excess lithium aluminium hydride is destroyed with a small amount of ethyl acetate; water and 2N HCl are added, the mixture is extracted and evaporated. Residue (1 g) is obtained in this manner. This is eluted over 90 g of silica gel 60 (230–400 mesh) with 10% and 20% ether in hexane. Hydrocarbon XI (225 g) and 150 mg of (−)I‴ are obtained in this manner. The hydrocarbon (−)XI is repeatedly chromatographed over silica gel 60 (0.04–0.063) 10% AgNO$_3$. 70 mg of pure (−)XI are obtained in this manner.

Spectral data of (−)XI

IR (liquid): 1635, 870, 810 cm$^{-1}$. UV (EtOH); λ max: 236, ε=13711. $^1$H-NMR (400 MHz, CDCl$_3$): 5.97(d,J=5.5,H-C(7) or H-C(8)); 5.915 (d,J=5.5,H-C(7) or H-C(8)); 4.837 (s,H-C(15)); 4.607 (s,H-C(15)); 0.938 (s,CH$_3$-C(5)), 0.807 (d,J=6.5,CH-C$_3$-C(10)); 0.707 (s,CH$_3$-C(5)); $^{13}$C-NMR (CDCl$_3$): 160.4 (s); 145.6 (d); 130.2 (d); 101.04 (t); 65.6 (s); 56.3 (s); 45.8 (s); 35.2 (s); 34.1 (t); 33.4 (t); 31 (t); 27.9 (q), 26.9 (q); 22.5 (t); 17.7 (q), 13.1 (q). MS: 216(23); 201(13); 188(1.6); 173(26); 159(14); 145(23); 134(100); 119(64); 105(35); 91(39); 77(11); 65(9); 55(19); 41(30); 32(10); 28(64). $[\alpha]_D^{20}$ (CHCl$_3$): $-102.5°$, c=1.034.

EXAMPLE 6

A mixture of (−)I′ and (−)I″ (16.6 g, 0.071 M) in the ratio 1/3.3 dissolved in 140 ml of toluene is treated dropwise at room temperature within 37 minutes with 72 ml (0.215 M) of sodium bis-(2-methoxyethoxy)aluminium dihydride (70% in toluene: "Fluka"). The reaction mixture is heated to 78° C., stirred for 23 hours 15 minutes, cooled to 6° C. and poured onto ice-water. 2N NaOH and ether are added and the mixture is stirred for 1 hour. The aqueous phase is washed with 2N HCl and saturated sodium chloride solution, dried and evaporated. The crude product (16.96 g) is distilled at 0.05 Torr. Product (8.65 g, 51.8%) of b.p. 92°–96° C. is obtained in this manner. This product contains (GC) 65% (−)I‴, 20% (−)I′ and 7% (−)I″. Compound I‴ can subsequently be purified by chromatography (silica gel 60, 0.04–0.063 mm) and elution with 5% ether/hexane.

Spectral data of (−)I‴

IR (liq) 1690, 1730 cm$^{-1}$. $^1$H-NMR (400 MHz, CDCl$_3$) 2.56 (m,J=9.6,J=9.6, J=6.8,H-C(9)); 2.43 (dd,J=20,J=9.6,H-C(8) anti to CH$_3$-C(9)); 2.04 (dd,J=20,J=9.6,H-C(8) syn to CH$_3$-C(9)); 1.06 (d,J=6.8,H$_3$-C(15)); 0.95 (s,H$_3$-C(14)); 0.92 (d,J=6.5,H$_3$-C(16)); 0.85 (s,H$_3$-C(13)); $^{13}$C-NMR (CDCl$_3$): 221.2 (s,C(7)); 66.6 (s,C(6)); 52.0 (s,C(1)); 43.8 (t,C(8)); 38.3 (d,C(10)); 36.1 (t,C(4)); 32.7 (s,C(5)); 31.6 (d,C(9)); 30.1 (t,C(11)); 27.4 (t,C(12)); 27.2 (q,C(13)); 24.5 (q,C(14)); 22.8 (t,C(2)); 17.2 (t,C(3)); 15.7 (q,C(16)); 15.4 (q,C(15)) $[\alpha]_D^{20} = -27.56$ (c=1.10, CHCl$_3$). MS: 234(42); 221(21); 203(3); 191(8); 179(100); 163(35); 151(69); 149(88); 133(51); 121(35); 109(49); 93(56); 81(63); 69(69); 55(39); 43(56). Odor of (−)I‴: ambergris, ambroxan.

EXAMPLE 7

From β,γ-monocyclo-homofarnesylic acid (Z/E: 1/2) (G. Lucius, Angew. Chem. (1956) 7, 247) there is obtained by treatment with tin tetrachloride in toluene (A. Saito, H. Matsushita, H. Kaneko, Chemistry Letters (1983), 729) at −20° C. or trifluoroacetic acid at 0° C. (EP-A 0 165 458) a mixture of (±)-episclareolid II″ and (±)-sclareolid II′ in the ratio 4/3. By treatment of this racemic mixture with polyphosphoric acid at 100° C. there are obtained the propellane derivatives (±)I′ and (±)I″ in the ratio ⅔ with 34% yield and the cyclopentenones (±)VII and (±)VIII in the ratio ¼ with 13% yield.

EXAMPLE 8

Polyphosphoric acid (150g) is heated to 100° C. A mixture of (±)-episclareolide II″ and (±)-sclareolide II′ (40 g in the ratio 4/3) is melted at 100° C. and added while stirring well. The mixture is left to react for 1 hour at 100°–110° C. while stirring intensively, then cooled to 70° C. and treated with water and hexane. It is cooled to room temperature while stirring, the phases are separated and the aqueous phase is extracted with ether. The combined organic phases are washed with saturated sodium chloride solution and with saturated bicarbonate solution, dried and evaporated. Crude product (29.1 g) is obtained in this manner. Distillation gives 1.26 g (34%) of a mixture of (±)I′ and (±)I″ in the ratio 1/2.5 (b.p. 65°–70° C. 1.5×10$^{-5}$ Torr) and 4.9 g (13%) of a mixture of (±)VII and (±)VIII in the ratio ¼ (b.p. 90°–95° C. 1.5×10$^{-5}$ Torr).

EXAMPLE 9

1S*,6R*,9S*,10S*-5,5,9,10-Tetramethyl-tricyclo-[4,3,3,0$^{1,6}$]dodecan-7-one (±)I‴

A mixture of (±)I′ and (±)I″ (37 g, 0.16 M) in the ratio 1/2.5 dissolved 140 ml of toluene is provided at room temperature and treated dropwise within 45 minutes with 137 ml (0.479M) of sodium bis-(2-methoxyethoxy)aluminium dihydride (70% in toluene). The reaction mixture is subsequently heated to 78° C., stirred for 41 hours, cooled to 6° C. and poured on to ice-water. NaOH (30%) and ether are added and the mixture is stirred for 1 hour. The aqueous phase is extracted with toluene, the organic phase is washed with 2N HCl and saturated sodium chloride solution, dried and evaporated. The crude product (37.4 g) is distilled at 21.5×10$^{-5}$ Torr. In this manner there are obtained 17 g (45%) of product, b.p. 75° C. This product contains (GC) 61% (±)I‴, 25% (±)I′ and 6% (±)I″.

In the following Examples A stands for the mixture containing

65% (−)I‴

20% (−)I′

7% (−)I′ and B stands for the mixture containing

61% (±)I‴

25% (±)I′

6% (±)I″

EXAMPLE 10

Composition for eau de toilette:

| Composition for eau de toilette: | |
|---|---|
| | Parts by weight |
| A or B | — 70.00 |
| Benzyl acetate | 40.00 40.00 |
| Geranyl acetate | 50.00 50.00 |
| Allyl amyl glycolate | 2.00 2.00 |
| Methyl anthranilate | 1.00 1.00 |
| Basil essence | 10.00 10.00 |
| Bergamotessence | 250.00 250.00 |
| Carbitol | 170.00 100.00 |
| Ceton alpha ™ (Givaudan) (but-3-en-2-one,4-(2,6,6-trimethyl-2-cyclohexen-1-yl-)3-methyl | 50.00 50.00 |
| Lemon essence (Argentinian) | 150.00 150.00 |
| Coumarin cryst. | 20.00 20.00 |
| Estragon essence | 5.00 5.00 |
| Fixolid ® (Givaudan) (7-acetyl-1,1,3,4,4,6-hexamethyltetralin) | 40.00 40.00 |
| Clove bud essence | 15.00 15.00 |
| Methyl dihydrojasmonate | 50.00 50.00 |
| Isoeugenol | 3.00 3.00 |
| Lavandin ess. | 100.00 100.00 |
| Evernyl ™ (Roure Bertrand) (benzoic acid,2,4-dihydroxy-3,6-dimethyl-,methyl ester) | 2.00 2.00 |
| Nutmeg essence | 20.00 20.00 |
| Gama-undecalactone | 2.00 2.00 |
| Sandalore ® (Givaudan) | 20.00 20.00 |

-continued

| Composition for eau de toilette: | | |
|---|---|---|
| | Parts by weight | |
| (5-(2,3,3-trimethylcyclopent-3-en-1-yl)3-methypentan-2-ol) | | |
| | 1000.00 | 1000.00 |

EXAMPLE 11

Formulation for cosmetics

| | Parts by weight | |
|---|---|---|
| A or B | — | 30.00 |
| Benzyl acetate | 100.00 | 100.00 |
| Geranyl acetate | 100.00 | 100.00 |
| Butylcyclohexyl acetate | 100.00 | 100.00 |
| Verdyl acetate ® (Givaudan) (inden-6-ol,4,7-methano-1H-3A,-4,5,6,7,7A-hexahydro-,acetate) | 20.00 | 20.00 |
| Phenylethyl alcohol | 150.00 | 150.00 |
| Hexyl cinnamaldehyde | 100.00 | 100.00 |
| Bergamot ess. (Calabrien) | 200.00 | 200.00 |
| Cyclohexylallyl propionate | 1.00 | 1.00 |
| Dimetol ® (Givaudan) (2,6-dimethylheptan-2-ol) | 20.00 | 20.00 |
| Dipropylene glycol | 30.00 | — |
| Gardenol TM (Givaudan) (acetic acid,1-phenylethyl ester) | 2.00 | 2.00 |
| Eugenol | 2.00 | 2.00 |
| Linalool synth. | 50.00 | 50.00 |
| Geranium oxide 10%/DIP | 5.00 | 5.00 |
| Petitgrain ess. Paraguay | 20.00 | 20.00 |
| Benzyl salicylate | 100.00 | 100.00 |
| | 1000.00 | 1000.00 |

The addition of A and, respectively, B in Example 10 and Example 11, which are characterized by a dry woody note (cedarwood) with a frankincense and amber impression, confers fullness and richness to the composition. The spicy note of the composition is rounded-off especially well.

We claim:

1. A compound of the formula

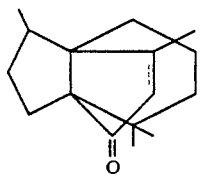

I wherein the dotted line represents an optional bond.

2. A compound according to claim 1 which is (±)1S*,6R*, 10S*-5,5,9,10-tetramethyl-tricyclo-[4,3,3,0$^{1,6}$]dodec-8-en-7-one.

3. A compound according to claim 1 which is (±)1S*,6R*, 10R*-5,5,9,10-tetramethyl-tricyclo-[4,3,3,0$^{1,6}$]dodec-8-en-7-one.

4. A compound according to claim 1 which is (±)1S*,6R*, 9S*,10S*-5,5,9,10-tetramethyl-tricyclo-[4,3,3,0$^{1,6}$]dodecan-7-one.

5. The compound according to claim 2 which is (−)1S,6R, 10S-5,5,9,10-tetramethyl-tricyclo-[4,3,3,0$^{1,6}$]dodec-8-en-7-one.

6. The compound according to claim 3 which is (−)1S,6R, 10R-5,5,9,10-tetramethyl-tricyclo-[4,3,3,0$^{1,6}$]dodec-8-en-7-one.

7. The compound according to claim 4 which is (−)1S,6R, 9S,10S-5,5,9,10-tetramethyl-tricyclo-[4,3,3,0$^{1,6}$]dodecan-7-one.

8. An odorant composition, which comprises an olfactorily effective amount of a compound of the formula

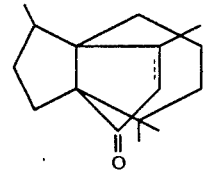

I wherein the dotted line signifies an optional bond, and at least one other olfactive agent.

9. An odorant composition according to claim 8 wherein the compound is (±)1S*,6R*,10S*-5,5,9,10-tetramethyl-tricyclo-[4,3,3,0$^{1,6}$]dodec-8-en-7-one.

10. An odorant composition according to claim 8 wherein the compound is (±)1S*,6R*,10R*-5,5,9,10-tetramethyl-tricyclo-[4,3,3,0$^{1,6}$]dodec-8-en-7-one.

11. An odorant composition according to claim 8 wherein the compound is (±)1S*,6R*,9S*,10S*-5,5,9,10-tetramethyl-tricyclo-[4,3,3,0$^{1,6}$]dodecan-7-one.

12. An odorant composition according to claim 9 wherein the compound is (−)1S,6R,10S-5,5,9,10-tetramethyl-tricyclo-[4,3,3,0$^{1,6}$]dodec-8-en-7-one.

13. An odorant composition according to claim 10 wherein the compound is (−)1S,6R,10R-5,5,9,10-tetramethyl-tricyclo-[4,3,3,0$^{1,6}$]dodec-8-en-7-one.

14. An odorant composition according to claim 11 wherein the compound is (−)1S,6R,9S,10S-5,5,9,10-tetramethyl-tricyclo-[4,3,3,0$^{1,6}$]dodecan-7-one.

15. A method for improving the odor of an odorant composition which comprises adding thereto an olfactorily effective amount of a compound of the formula

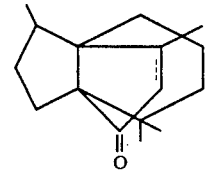

I wherein the dotted line signifies an optional bond.

16. A method according to claim 15 wherein the compound is (±)1S*,6R*,10S*-5,5,9,10-tetramethyl-tricyclo-[4,3,3,0$^{1,6}$]dodec-8-en-7-one.

17. A method according to claim 15 wherein the compound is (±)1S*,6R*,10R*-5,5,9,10-tetramethyl-tricyclo-[4,3,3,0$^{1,6}$]dodec-8-en-7-one.

18. A method according to claim 15 wherein the compound is (±)1S*, 6R, 9S*, 10S*-5,59,10-tetramethyl-tricyclo-[4,3,3,0$^{1,6}$]dodecan-7-one.

19. A method according to claim 16 wherein the compound is (−)1S, 6S,10S-5,5,9,10-tetramethyl-tricyclo-[4,3,3,0$^{1,6}$]-dodec-8-en-7-one.

20. A method according to claim 17 wherein the compound id (−)1S,6R,10R-5,5,9,10tetramethyl-tricyclo-[4,3,3,0$^{1,6}$]dodecan-7-one.

21. A method according to claim 18 wherein the compound is (−)1S,6R,10R-5,5,9,10-tetramethyl-tricyclo-[4,3,3,0$^{1,6}$]dodecan-7-one.

22. A process for the manufacture of a compound of the formula

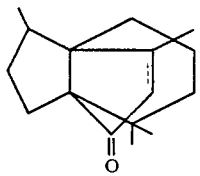

I which process comprises
a) rearranging sclareolide, episclareolide or isosclareolide in the presence of polyphosphoric acid or P$_2$O$_5$/methanesulphonic acid, at an elevated temperature with dehydration and, if desired,
b) reducing the carbon-carbon double bond present in the reaction product, wherein sodium bis-(2-methoxyethoxy)-aluminum hydride is used as the reducing agent.

* * * * *